United States Patent [19]
Blanchard et al.

[11] Patent Number: 4,464,377
[45] Date of Patent: Aug. 7, 1984

[54] ANTI-THROMBOTIC THERAPEUTIC COMPOSITIONS

[76] Inventors: Jean Blanchard; Edouard Panak, both of 73 Ave. Raymond Naves, 31500 Toulouse, France

[21] Appl. No.: 292,241

[22] Filed: Aug. 12, 1981

Related U.S. Application Data

[63] Continuation of Ser. No. 108,652, Dec. 31, 1979, abandoned, which is a continuation-in-part of Ser. No. 917,374, Jun. 20, 1978, Pat. No. 4,210,649.

[30] Foreign Application Priority Data

Jun. 22, 1977 [FR] France ............................... 77 19161
Dec. 29, 1978 [GB] United Kingdom ............... 50360/78

[51] Int. Cl.³ ........................................... A61K 31/435
[52] U.S. Cl. ................................................... 424/256
[58] Field of Search ......................................... 424/256

[56] References Cited

U.S. PATENT DOCUMENTS 4,051,141 9/1977 Castaigne ............................. 424/256
4,071,630 1/1978 Wiskott et al. ....................... 424/256
4,097,482 6/1978 Amselem ............................. 424/256

OTHER PUBLICATIONS

*The Merck Index,* Ninth Ed. 1976, 7628, Merck & Co., Inc., Rahway, N.J.

*Primary Examiner*—Frederick E. Waddell
*Attorney, Agent, or Firm*—Weiser & Stapler

[57] ABSTRACT

This invention relates to therapeutic compositions comprising, as active ingredients, a combination of a pyridine derivative having an anti-blood-platelet-aggregation activity with a derivative having beta-blocking properties, which exhibit synergistic anti-thrombotic activity.

6 Claims, No Drawings

ANTI-THROMBOTIC THERAPEUTIC COMPOSITIONS

This application is a continuation of application Ser. No. 108,652, filed Dec. 31, 1979, now abandoned, which is a continuation-in-part application based on our co-pending U.S. patent application Ser. No. 917,374, filed June 20, 1978, now U.S. Pat. No. 4,210,649.

This invention relates to therapeutic compositions having an antithrombotic activity comprising, as active ingredients, a combination of a derivative having anti-blood-platelet-aggregating properties and of a derivative having beta-receptor blocking properties.

The derivative having anti-blood-platelet-aggregating properties is selected from the pyridine compounds having the formula:

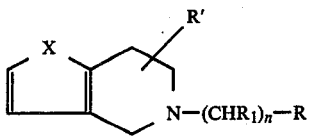

in which:

X represents oxygen or sulfur;

R represents a phenyl or benzoyl group which may carry one or more substituents selected from halogen atoms and the straight- or branched-chain lower alkyl groups, the straight- or branched-chain lower alkoxy groups, the nitro, amino, sulfonylamino, carboxy, lower alkoxycarbonyl, cyano, phenyl, hydroxy(lower)alkyl, methylene-dioxy and ethylene-dioxy groups; an alpha-naphthyl group or a thienyl group;

$R_1$ represents a hydrogen or halogen atom or a hydroxy group, a straight- or branched-chain lower alkyl group, a straight- or branched-chain lower alkoxy group, or a phenyl group;

R' repesents a lower alkyl group; and n is an integer from 1 to 15;

and the symbols $R_1$ may have different meanings in each radical $CHR_1$ when n is greater than 1;

and the pharmaceutically acceptable acid addition salts and quaternary ammonium derivatives of said compounds.

The terms "lower alkyl group" and "lower alkoxy group" are intended to mean groups having 1–6 carbon atoms and particularly 1–4 carbon atoms.

Non-limiting Examples of derivatives of the formula (I) useful in the therapeutic composition of this invention include:

5-(2-chloro-benzyl)-4,5,6,7-tetrahydro-thieno[3,2-c]pyridine, (ticlopidine);
5-(3,4,5-trimethoxy-benzyl)-4,5,6,7-tetrahydro-thieno[3,2-c]pyridine;
5-(4-methoxy-benzyl)-4,5,6,7-tetrahydro-thieno[3,2-c]pyridine;
5-(2-hydroxy-2-phenyl-ethyl)-4,5,6,7-tetrahydro-thieno[3,2-c]pyridine;
5-p-chlorobenzyl-4,5,6,7-tetrahydro-thieno[3,2-c]pyridine;
5-p-chlorobenzyl-4,5,6,7-tetrahydro-furo[3,2-c]pyridine;
5-(3,5-dimethoxy-benzyl)-4,5,6,7-tetrahydro-thieno[3,2-c]pyridine;
5-(3,4,5-trimethoxy-benzyl)-4,5,6,7-tetrahydro-furo[3,2-c]pyridine;
5-(3-methoxy-benzyl)-4,5,6,7-tetrahydro-thieno[3,2-c]pyridine;
5-(3-methyl-benzyl)-4,5,6,7-tetrahydro-furo[3,2-c]pyridine;
5-(4-methyl-benzyl)-4,5,6,7-tetrahydro-furo[3,2-c]pyridine;
5-(2-fluoro-benzyl)-4,5,6,7-tetrahydro-thieno[3,2-c]pyridine;
5-(3,4-dichloro-benzyl)-4,5,6,7-tetrahydro-thieno[3,2-c]pyridine;
5-(2-phenyl-ethyl)-4,5,6,7-tetrahydro-thieno[3,2-c]pyridine;
5-(2-phenyl-ethyl)-4,5,6,7-tetrahydro-furo[3,2-c]pyridine;
5-(1-methyl-2-hydroxy-2-phenyl-ethyl)-4,5,6,7-tetrahydro-thieno[3,2-c]pyridine;
5-(2-methyl-benzyl)-4,5,6,7-tetrahydro-thieno[3,2-c]pyridine;
5-(3-methyl-benzyl)-4,5,6,7-tetrahydro-thieno[3,2-c]pyridine;
5-(4-methyl-benzyl)-4,5,6,7-tetrahydro-thieno[3,2-c]pyridine;
5-(4-fluoro-benzyl)-4,5,6,7-tetrahydro-thieno[3,2-c]pyridine;
5-(2,6-dichloro-benzyl)-4,5,6,7-tetrahydro-thieno[3,2-c]pyridine;
5-(2-nitro-benzyl)-4,5,6,7-tetrahydro-thieno[3,2-c]pyridine;
5-(4-hydroxy-benzyl)-4,5,6,7-tetrahydro-thieno[3,2-c]pyridine;
5-(2-p-hydroxyphenyl-2-hydroxy-ethyl)-4,5,6,7-tetrahydro-thieno[3,2-c]pyridine;
5-(2-p-methoxyphenyl-2-hydroxy-ethyl)-4,5,6,7-tetrahydro-thieno[3,2-c]pyridine;
5-(2-p-chloroyphenyl-2-hydroxy-ethyl)-4,5,6,7-tetrahydro-thieno[3,2-c]pyridine;
5-(2-hydroxy-2-o-methoxyphenyl-ethyl)-4,5,6,7-tetrahydro-thieno[3,2-c]pyridine;
5-(2-hydroxy-2-m-methoxyphenyl-ethyl)-4,5,6,7-tetrahydro-thieno[3,2-c]pyridine;
5-(3-o-chloroyphenyl-3-hydroxy-propyl)-4,5,6,7-tetrahydro-thieno[3,2-c]pyridine;
5-(1-phenyl-ethyl)-4,5,6,7-tetrahydro-thieno[3,2-c]pyridine;
5-(3-hydroxy-3-p-nitrophenyl-propyl)-4,5,6,7-tetrahydro-thieno[3,2-c]pyridine;
5-(3-hydroxy-3-phenyl-propyl)-4,5,6,7-tetrahydro-thieno[3,2-c]pyridine;
5-(2-benzoyl-ethyl)-4,5,6,7-tetrahydro-thieno[3,2-c]pyridine;
5-o-bromobenzyl-4,5,6,7-tetrahydro-thieno[3,2-c]pyridine;
5-p-nitrobenzyl-4,5,6,7-tetrahydro-thieno[3,2-c]pyridine;
5-(3-chloro-benzyl)-4,5,6,7-tetrahydro-thieno[3,2-c]pyridine;
5-(3-hydroxy-benzyl)-4,5,6,7-tetrahydro-thieno[3,2-c]pyridine;
5-(2-p-fluoroyphenyl-2-hydroxy-ethyl)-4,5,6,7-tetrahydro-thieno[3,2-c]pyridine;
5-(2,5-dimethoxy-2-phenyl-2-hydroxy-ethyl)-4,5,6,7-tetrahydro-thieno[3,2-c]pyridine;
5-(2,3,4-trimethoxy-benzyl)-4,5,6,7-tetrahydro-thieno[3,2-c]pyridine;
5-benzyl-4,5,6,7-tetrahydro-thieno[3,2-c]pyridine;
5-(2-methoxy-benzyl)-4,5,6,7-tetrahydro-thieno[3,2-c]pyridine;

5-(3,4-dimethoxy-benzyl)-4,5,6,7-tetrahydro-thieno[3,2-c]pyridine;
5-[3-(4-fluoro-benzoyl)-propyl]-4,5,6,7-tetrahydro-thieno[3,2-c]pyridine;
5-o-methoxycarbonylbenzyl-4,5,6,7-tetrahydro-thieno[3,2-c]pyridine;
5-o-carboxybenzyl-4,5,6,7-tetrahydro-thieno[3,2-c]pyridine;
5-o-methoxycarbonylbenzyl-6-methyl-4,5,6,7-tetrahydro-thieno[3,2-c]pyridine;
5-(α-naphthyl-methyl)-4,5,6,7-tetrahydro-thieno[3,2-c]pyridine;
5-[(5-chloro-2-thienyl)methyl]-4,5,6,7-tetrahydro-thieno[3,2-c]pyridine;
5-[2-hydroxy-2-(2-thienyl)-ethyl]-4,5,6,7-tetrahydro-thieno[3,2-c]pyridine;
5-o-cyanobenzyl-4,5,6,7-tetrahydro-thieno[3,2-c]pyridine;
5-(3,4-methylenedioxy-benzyl)-4,5,6,7-tetrahydro-thieno[3,2-c]pyridine;
5-[2-(4-bis-phenyl)-2-hydroxy-ethyl]-4,5,6,7-tetrahydro-thieno[3,2-c]pyridine;
5-o-hydroxy-methylbenzyl-4,5,6,7-tetrahydro-thieno[3,2-c]pyridine;
5-benzhydryl-4,5,6,7-tetrahydro-thieno[3,2-c]pyridine;
5-(1-o-chlorophyenyl-butyl)-4,5,6,7-tetrahydro-thieno[3,2-c]pyridine;
5-(1-o-chlorophyenyl-pentyl)-4,5,6,7-tetrahydro-thieno[3,2-c]pyridine;
5-(1-o-chlorophyenyl-propyl)-4,5,6,7-tetrahydro-thieno[3,2-c]pyridine;
5-(1-o-chlorobenzyl-ethyl)-4,5,6,7-tetrahydro-thieno[3,2-c]pyridine;
5-(1-phenyl-ethyl)-4,5,6,7-tetrahydro-thieno[3,2-c]pyridine;

The derivatives having beta-blocking properties are selected from the following compounds of the formulas (II) and (III) and their pharmaceutically acceptable inorganic or organic acid addition salts.

A first family of compounds of this type is that represented by the formula (II)

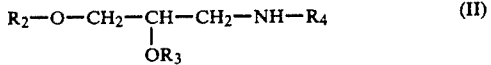

in which:
R₂ represents a mono- or polycyclic, carbo- or heterocyclic radical having at least one ring of aromatic character, and which is attached to the oxygen atom by a ring carbon atom, preferably of the aromatic ring;
R₃ is hydrogen or the acyl radical of an organic carboxylic acid; and
R₄ represents a substituted or unsubstituted aliphatic, cyclo-aliphatic or araliphatic hydrocarbon radical;
and derivatives thereof, including the pharmaceutically acceptable inorganic or organic acid addition salts thereof.

The carbocyclic radicals R₂ are typically phenyl radicals, and also optionally partly saturated bicyclic (e.g., naphthyl, indanyl) or polycyclic (e.g., fluorene) radicals.

The heterocyclic radicals R₂ may contain one or more nitrogen, oxygen or sulfur atoms. They are optionally partly saturated monocyclic (pyridyl, pyrimidyl) or bicyclic (indolyl, quinolyl) radicals.

Said radicals R₂ may be substituted with at least an optionally substituted aliphatic or cycloaliphatic hydrocarbon radical, an optionally esterified or etherified hydroxy or mercapto group, or an acyl, carboxy, nitro, optionally substituted amino, or oxo group.

The acyl radicals R₃ are typically the corresponding radicals of the organic carboxylic acids, particularly lower alkanoyl or benzoyl.

The aliphatic hydrocarbon radicals R₄ are typically straight- or branched-chain lower alkyl groups; the cycloaliphatic radicals are typically cycloalkyl groups, and the araliphatic radicals are typically lower phenylalkyl groups.

Non-limiting Examples of compounds of the formula (II) useful in the therapeutic composition of this invention are given below:
1-isopropylamino-3-[(1)-naphthyloxy]-2-propanol (propranolol);
(±)1-isopropylamino-3-[4-(2-methoxy-ethyl)-phenoxy]-2-propanol (metoprolol);
2-[4-(2-hydroxy-3-isopropylamino-propoxy)-phenyl]acetamide (atenolol);
3'-acetyl-4'-(2-hydroxy-3-isopropylamino-propoxy)-butyranilide (acebutolol);
1-(4-indolyl-oxy)-3(isopropylamino)-2-propanol (pindolol);
(−)-1-tert-butylamino)-3-[3-(4-morpholino-1,2,5-thiadiazol-3-yl)oxy]-2-propanol (timolol);
1-(tert-butylamino)-3-(2-chloro-5-methyl-phenoxy)-2-propanol (bupranolol);
(±)-5-[3-tert-butylamino)-2-hydroxy-propoxy]3,4-dihydro-2H-naphthalenone (bunolol);
1-(2'-allyl-phenoxy)-3-isopropylamino-2-propanol (alprenolol); and
1-(2-allyloxy-phenoxy)-3-isopropylamino-2-propanol (oxprenolol).

The second family of the compounds having beta-blocking properties is that represented by the formula (III)

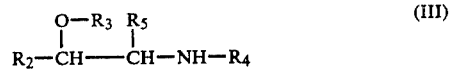

in which R₂, R₃, and R₄ have the meanings given for the formula (II) and R₅ is hydrogen or a lower alkyl radical, and their pharmaceutically acceptable inorganic or organic acid addition salts.

The compounds of the formula (III) useful in the therapeutic composition of this invention include particularly:
2-isopropylamino-1-(1-naphthyl)-ethanol;
2-tert-butylamino-1-(2,5-dimethoxy-phenyl)-ethanol;
1-(3,4-dichlorophenyl)-2-isopropylamino-ethanol;
2-isopropylamino-1-(4-nitro-phenyl)-propanol;
2-isopropylamino-1-(methylsulfonylaminophenyl)-ethanol;
1-(4-carbamoyl-3-hydroxyphenyl)-2-tert-butylamino-ethanol; and
2-tert-butylamino-1-(1,2,3,4-tetrahydro-5-naphthyl)-ethanol.

The combinations of active ingredients employed in the therapeutic compositions of this invention exhibit a synergistic effect which will be evidenced by means of the following illustrative Example which gives the results of a toxicological and pharmacological investigation effected with compositions of this invention comprising, as the compound having anti-blood-plateletaggregating properties, ticlopidine hydrochloride having the formula:

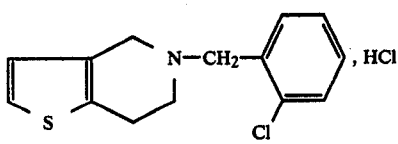

and, as compounds having beta-blocking properties:
(a) propranolol having the formula:

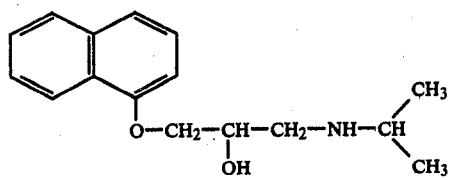

(b) acebutolol having the formula:

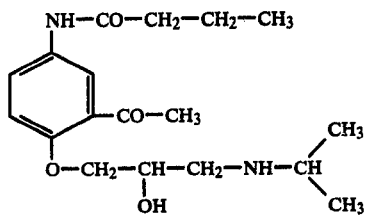

(c) metoprolol having the formula:

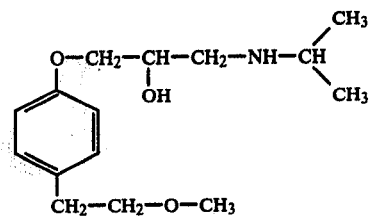

and (d) atenolol having the formula:

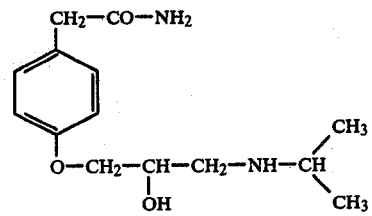

I. TOXICOLOGICAL INVESTIGATION

This investigation included determinations of:
1. Acute toxicity of ticlopidine hydrochloride, ($LD_{50}$ rat/kg: p.o. 1938 mg; i.p. 291 mg; $LD_{50}$ mice/kg p.o. 777 mg; i.p. 532 mg), of propranolol; ($LD_{50}$/kg: p.o. 35 mg in the male and 45 mg in the female), of metoprolol ($LD_{50}$ rat/kg: p.o. 4070 mg; i.v. 70.1 mg; $LD_{50}$ mice/kg: p.o. 2380 mg; i.v. 74.6 mg), of acebutolol and of atenolol ($LD_{50}$ rat/kg: p.o. 3000 mg; i.v. >50-60 mg; $LD_{50}$ mice/kg: p.o. >2000 mg, i.v. >100 mg) and of the combinations thereof of this invention.
2. Chronic and delayed toxicity.
3. Local and systemic tolerance.

It was found that the compositions of this invention, on administration by gastric intubation, are perfectly tolerated, under the condition of the experiment without inducing any local or systemic reaction.

The toxicities of the compositions of this invention are the same as that of their components and, this respect, no potentation phenomenon was found to occur.

II. PHARMACOLOGICAL INVESTIGATION

This investigation concerned myocardial necrosis induced in animals under severe stress conditions which may be reproduced by infusion of adrenalin.

Mongrel dogs of either sex, weighing about 10 kg, were distributed into 15 groups of 5 animals each: except for one group of untreated dogs (controls, Group 1), the other groups were orally administered a test material, twice a day, for 4 days, repsectively:
Group 2: 50 mg/kg ticlopidine hydrochloride
Group 3: 100 mg/kg ticlopidine hydrochloride
Group 4: 50 mg/kg ticlopidine hydrochloride+5 mg/kg propranolol
Group 5: 100 mg/kg ticlopidine hydrochloride+10 mg/kg propranolol
Group 6: 50 mg/kg ticlopidine hydrochloride+25 mg/kg acebutolol
Group 7: 100 mg/kg ticlopidine hydrochloride+50 mg/kg acebutolol
Group 8: 50 mg/kg ticlopidine hydrochloride+10 mg/kg metoprolol
Group 9: 100 mg/kg ticlopidine hydrochloride+20 mg/kg metoprolol
Group 10: 50 mg/kg ticlopidine hydrochloride+5 mg/kg atenolol
Group 11: 100 mg/kg ticlopidine hydrochloride+10 mg/kg atenolol
Group 12: 10 mg/kg propranolol
Group 13: 50 mg/kg acebutolol
Group 14: 20 mg/kg metoprolol
Group 15: 10 mg/kg atenolol Eighteen hours after the last treatment the dogs were anesthetized with phenobarbital (25 mg/kg, i.v.); a catheter was placed in the femoral artery, the blood pressure was recorded via a STAHAM P 23 GD sensor and the ECG was recorded ($D_1$ and $D_2$) with a RACIA polygraph. The adrenalin was infused by the cephalic route at a dosage of 4 μg/kg/mn at a rate of 2 ml/mr for 4 hours.

Arterial blood samples were taken before and after the end of the infusion, to effect the blood-platelet counts.

The animals were freed from the catheters and were allowed to wake up. The animals which survived 7 days later were sacrificed and autopsied; the hearts were cut out and examined macroscopically prior to taking samples for histological examination. Any macroscopic anomalies are rated according to the following code (Table I) which was established arbitrarily and which takes into account the extent of the damages (p. 13).

TABLE I

| Parts observed | Extent of the involvement | Entirely hemmoragic | Large hemorragic areas | Numerous hemmoragic points | Some hemmoragic points | Small hemmoragic or necrotic point |
| --- | --- | --- | --- | --- | --- | --- |
| Exterior | Percardium | 5 | 4 | 3 | 2 | 1 |
| | Left ventricle | 5 | 4 | 3 | 2 | 1 |
| | Right ventricle | 5 | 4 | 3 | 2 | 1 |
| | Left auricle | 5 | 4 | 3 | 2 | 1 |
| | Right auricle | 5 | 4 | 3 | 2 | 1 |
| Cavities | Left ventricle | 5 | 4 | 3 | 2 | 1 |
| | Right ventricle | 5 | 4 | 3 | 2 | 1 |
| | Left auricle | 5 | 4 | 3 | 2 | 1 |
| | Right auricle | 5 | 4 | 3 | 2 | 1 |

The following results were obtained:

Blood-platelet count

The blood-platelet count effected immediately prior to and after adrenalin infusion shows a 32.4% decrease in the controls (Group 1). In contrast, in the treated animals, the count tends to increase, with the exception, however, of those which were administered only beta-blocking compounds:
Group 2: +14.0%
Group 3: +13.2%
Group 4: +18.0%
Group 5: +20.0%
Group 6: +17.0%
Group 7: +19.5%
Group 8: +15.1%
Group 9: +16.8%
Group 10: +16.5%
Group 11: +18.2%
Group 12: −20.0%
Group 13: −24.1%
Group 14: −17.4%
Group 15: −27.6%

Survival Time

The number of animals that survived on the 7th day after adrenalin perfusion is reported below:
Group 1: 2/5
Group 2: 3/5
Group 3: 4/5
Group 4: 4/5
Group 5: 5/5
Group 6: 4/5
Group 7: 5/5
Group 8: 4/5
Group 9: 5/5
Group 10: 4/5
Group 11: 5/5
Group 12: 2/5
Group 13: 2/5
Group 14: 2/5
Group 15: 2/5

Macroscopic Lesions

It is found that the treated animals reach necrosis scores calculated according to the above Table) of a markedly lesser magnitude than the controls; the necrosis scores of the animals administered only beta-blocking compounds are substantially identical with those of the controls:
Group 1: 18.0
Group 2: 6.8
Group 3: 4.8
Group 4: 2.8
Group 5: 2.2
Group 6: 3.7
Group 7: 3.4
Group 8: 3.0
Group 9: 1.8
Group 10: 2.6
Group 11: 1.0
Group 12: 15.4
Group 13: 19.6
Group 14: 16.1
Group 15: 13.4

It may be concluded, from the set of results obtained, that intravenous perfusion of adrenalin induces in the controls serious disorders which are essentially shown by a drop of the number of blood-platelets and by a myocardial involvement of necrotic type. In contrast, pretreatment with ticlopidine hydrochloride provides significant protection against myocardia necrosis, improves the survival time and increases the number of blood-platelets. Said results are enhanced when ticlopidine hydrochloride is combined with a beta-blocking material, both products thus functioning according to a synergistic effect. It should be noted that the beta-blocking materials, when administered individually, have no effect on the blood-platelet count which is found to decrease, on the survival time which is identical with that of the controls, and on the macroscopic lesions which are substantially identical with those of the controls.

The pharmacological investigation reported above shows the usefulness of the combination of a compound having anti-blood-platelet-aggregating properties with a compound having beta-blocking properties, said combinations exhibiting valuable antithrombotic properties.

In view of this antithrombotic activity, the combination of this invention may be advantageously used in human and veterinary medicine.

The active ingredients are generally used together with a therapeutically administrable carrier. Thus, the composition of this invention may advantageously be formulated as tablets, coated tablets or capsules for oral administration, and as suppositories for rectal administration. Generally, each unit dose will contain 0.05–0.200 g of anti-blood-platelet-aggregating material and 0.010–0.150 g of beta-blocking material. The daily dosage regimen may vary from 0.05 g to 1 g for the anti-blood-platelet-aggregating material and from 0.010 g to 0.600 g for the beta-blocking material.

Non-limiting Examples of pharmaceutical formulations of the compositions of this invention are given below:

1. Tablets

Ticlopidine hydrochloride    0.200 g

| -continued | |
|---|---|
| Propranolol | 0.030 g |
| Excipients: starch, lactose, stearic acid, talc, sufficient to make one 0.400 g tablet. | |
| 2 Coated Tablets | |
| Ticlopidine hydrochloride | 0.150 g |
| Acebutolol | 0.150 g |
| Excipients: corn starch, dicalcium phosphate, shellac, gelatin, granulated sugar, talc, titanium dioxide, carnauba wax, sufficient to made one 0.650 g coated tablet. | |
| 3. Capsules | |
| Ticlopidine hydrochloride | 0.180 g |
| Propranolol | 0.025 g |
| Excipients: stearic acid, talc, sufficient to make one capsule. | |
| 4. Capsules | |
| Ticlopidine hydrochloride | 0.150 g |
| Acebutolol | 0.150 g |
| Excipients: talc, stearic acid, sufficient to make one capsule. | |
| 5. Capsules | |
| Ticlopidine hydrochloride | 0.200 g |
| Metoprolol | 0.150 g |
| Excipients: talc, lactose, sufficient to make one capsule. | |
| 6. Capsules | |
| Ticlopidine hydrochloride | 0.180 g |
| Atenolol | 0.025 g |
| Excipients: talc, stearic acid, sufficient to make one capsule. | |

In view of their antithrombotic properties, the compositions of this invention reduce the risk of accidents in patients suffering from thrombo-embolic diseases.

Therefore, the compositions are applicable for preventive or curative purposes, in accidents related to a thrombotic process, particularly when the latter involves the blood-platelets in their development; the compositions of this invention are particularly useful in patients in which there is a risk of development or of relapse of a coronary or cerebral ischemic accident or of any vascular ischemic episode.

What is claimed is:

1. A prophylactic and therapeutic anti-thrombotic composition comprising a biologically acceptable carrier and an effective amount of the combination of a compound having beta-blocking properties and ticlopidine or the pharmaceutically acceptable salts thereof, said beta-blocking compounds being selected from the group consisting of a compound of the formula:

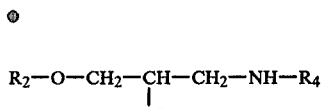

and

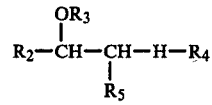

in which:

$R_2$ is selected from the group consisting of phenyl, naphthyl, indanyl, fluorene, morpholinyl, pyridyl, pyrimidyl, indolyl, quinolyl and the mercapto, acyl, carboxy, nitro or amino substituted groups thereof, $R_3$ is selected from the group consisting of hydrogen, lower alkanoyl and benzoyl, $R_4$ is selected from the group consisting of lower alkyl, cycloloweralkyl, and phenyl lower alkyl, and $R_5$ is selected from the group consisting of hydrogen and lower alkyl; and the pharmaceutically acceptable salts thereof.

2. The composition of claim 1 wherein said beta-blocking compound is selected from the group consisting of:
1-isopropylamino-3-[(1)-naphthyloxy]-2-propanol;
(±)1-isopropylamino-3-[4-(2-methoxy-ethyl)-phenoxy]-2-propanol;
2-[4-(2-hydroxy-3-isopropylamino-propoxy)-phenyl]acetamide;
3'-acetyl-4'-(2-hydroxy-3-isopropylamino-propoxy)-butyranilide;
1-(4-indolyl-oxy)-3(isopropylamino)-2-propanol;
(−)-1-tert-butylamino)-3-[3-(4-morpholino-1,2,5-thiadiazol-3-yl)oxy]-2-propanol;
1-(tert-butylamino)-3-(2-chloro-5-methyl-phenoxy)-2-propanol;
(±)-5-[3-tert-butylamino)-2-hydroxy-propoxy]3,4-dihydro-2H-naphthalenone;
1-(2'-allyl-phenoxy)-3-isopropylamino-2-propanol; and
1-(2-allyloxy-phenoxy)-3-isopropylamino-2-propanol.

3. The composition of claim 1 wherein said beta-blocking compound is selected from the group consisting of:
2-isopropylamino-1-(1-naphthyl)-ethanol;
2-tert-butylamino-1-(2,5-dimethoxy-phenyl)-ethanol;
1-(3,4-dichlorophenyl)-2-isopropylamine-ethanol;
2-isopropylamino-1-(4-nitro-phenyl)-propanol;
1-(4-carbamoyl-3-hydroxyphenyl)-2-tert-butylamino-ethanol; and
2-tert-butylamino-1-(1,2,3,4-tetrahydro-5-naphthyl)-ethanol or 2-isopropylamino-1-(methylsulfonylaminophenyl)-ethanol.

4. The composition of any one of claims 2 or 3 wherein the ticlopidine is a hydrochloride salt.

5. The composition of claim 1 containing about 0.05 to about 0.2 g of ticlopidine and about 0.01 to about 0.15 g of said beta-blocking compound.

6. A method for the prevention or treatment of thrombosis in a patient which comprises administering to said patient in an amount effective to prevent or treat such thrombosis, an effective amount of the composition of any one of claims 2, 3, 5 or 1.

* * * * *

UNITED STATES PATENT AND TRADEMARK OFFICE
CERTIFICATE OF CORRECTION

PATENT NO.  : 4,464,377
DATED       : August 7, 1984
INVENTOR(S) : Jean Blanchard, et al It is certified that error appears in the above-identified patent and that said Letters Patent is hereby corrected as shown below:

On the title page the following should be added:

-- [73] Assignee:   Sanofi,
                    Paris, France --.

Signed and Sealed this

Thirtieth Day of April 1985

[SEAL]

Attest:

DONALD J. QUIGG

Attesting Officer   Acting Commissioner of Patents and Trademarks